US010166167B2

(12) United States Patent
Lieberman et al.

(10) Patent No.: US 10,166,167 B2
(45) Date of Patent: Jan. 1, 2019

(54) FINGER VIBRATOR

(71) Applicant: Mating Components, LLC, Brooklyn, NY (US)

(72) Inventors: Janet Lieberman, Brooklyn, NY (US); Josh Nalven, Brooklyn, NY (US); David Block, Brooklyn, NY (US); Alexandra Fine, Brooklyn, NY (US); Amanda Couto, Pembroke Pines, FL (US)

(73) Assignee: Mating Components, LLC, Brooklyn, NY (US)

( * ) Notice: Subject to any disclaimer, the term of this patent is extended or adjusted under 35 U.S.C. 154(b) by 174 days.

(21) Appl. No.: 15/341,503

(22) Filed: Nov. 2, 2016

(65) Prior Publication Data

US 2018/0116904 A1 May 3, 2018

(51) Int. Cl.

| | |
|---|---|
| ***A61F 5/00*** | (2006.01) |
| ***A61H 19/00*** | (2006.01) |
| ***A61H 23/02*** | (2006.01) |

(52) U.S. Cl.

CPC ............ *A61H 19/34* (2013.01); *A61H 19/30* (2013.01); *A61H 23/02* (2013.01); *A61H 2201/0153* (2013.01); *A61H 2205/087* (2013.01)

(58) Field of Classification Search

CPC ........ A61H 19/00; A61H 19/30; A61H 19/34; A61H 19/40; A61H 21/00; A61H 2201/0153

USPC ........................... 600/38-41; 601/46, 72, 80

See application file for complete search history.

(56) References Cited

U.S. PATENT DOCUMENTS

| | | | | |
|---|---|---|---|---|
| 2,918,055 A | 12/1959 | Boerger | | |
| 3,585,990 A | 6/1971 | Blachly et al. | | |
| 4,116,233 A | 9/1978 | Scaduto | | |
| 5,601,529 A | 2/1997 | Wollman | | |
| 6,203,509 B1 | 3/2001 | Duboff | | |
| 6,748,604 B2 | 6/2004 | Duboff et al. | | |
| 7,435,889 B1 | 10/2008 | Heidt | | |
| 8,033,985 B2 | 10/2011 | Smith | | |
| 9,132,058 B2 * | 9/2015 | Imboden | ................ | A61H 19/00 |
| 2003/0181835 A1 | 9/2003 | Klein | | |
| 2004/0020241 A1 | 2/2004 | Boiadjian | | |
| 2012/0116273 A1 | 5/2012 | Nan | | |
| 2016/0361221 A1 * | 12/2016 | Ebbers | .................. | A61H 1/008 |

* cited by examiner

*Primary Examiner* — John Lacyk

(74) *Attorney, Agent, or Firm* — Roy L. Chan, A Professional Law Corporation; Roy Chan

(57) ABSTRACT

The present invention relates to vibrating devices for applying vibrations to body parts, particularly for female stimulation, and more particularly to the field of sexual stimulation of the clitoris. One embodiment is a device for applying vibration to a body part of a user, the device comprising: a vibrator mechanism; and, a body enclosing the vibrator mechanism, wherein the body comprises a first portion and a second portion; wherein the body and the vibrator mechanism are configured to allow the first portion to provide a first vibratory sensation to the user when the first portion is applied to the body part; and, wherein the body and the vibrator mechanism are configured to allow the second portion to provide a second vibratory sensation to the user when the second portion is applied to the body part.

12 Claims, 16 Drawing Sheets

FINGER VIBRATOR

CROSS-REFERENCE TO RELATED APPLICATIONS

Not Applicable

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISC APPENDIX

Not Applicable

BACKGROUND OF THE INVENTION

This invention relates to vibrating devices for applying vibrations to body parts, particularly for female stimulation, and more particularly to the field of sexual stimulation of the clitoris. Vibrating electromechanical devices, sometimes referred to as vibrators, can be used to help facilitate women reaching orgasm. Conventional vibrators, and particularly sexual stimulation apparatus often do not include a convenient handle and are thus difficult for the user to grip it comfortably during use. Conventional vibrators that include a handle, usually require the user to grasp and hold the handle while applying vibration to a body part, such as during stimulation of the clitoris. Thus, a user may experience tension, fatigue, or discomfort in their wrist, arm, or shoulder while using a conventional vibrator. Moreover, when using a conventional vibrator for sexual stimulation, the hand or fingers of the user may reflexively relax causing the vibrator to slip and change its position relative to the stimulated body part, or fall altogether, resulting in reduction of sexual stimulation. This can be particularly problematic for female users when using vibrators for sexual stimulation at least in part because of the anatomical position of a woman's vagina in relation to their arms and hands.

Without a handle, or with only a single handle, a conventional vibrator is difficult to hold comfortably by a user while accurately controlling the position and pressure of the vibrator over a body part. It is particularly difficult for a female user to keep her wrist and fingers in a natural and comfortable orientation, or even relaxed, while using a conventional vibrator for sexual stimulation. The present invention aims at solving these problems for female and other users.

BRIEF SUMMARY OF THE INVENTION

The present invention relates to devices and methods for producing stimulation to a body part of a user, particularly a clitoris, by inserting fingers through a tether and allowing the fingers to engage a vibrating portion of the device for added stability and control of the device. Many of the embodiments of devices and methods of the present invention are also compatible with sexual intercourse because their configuration allows stimulation to be provided to the clitoris while allowing the vaginal opening to remain accessible.

In an embodiment of the present invention, a device for applying vibration to a body part of a user is provided, the device comprising: a vibrator mechanism; and, a body enclosing the vibrator mechanism, wherein the body comprises a first portion and a second portion; wherein the body and the vibrator mechanism are configured to allow the first portion to provide a first vibratory sensation to the user when the first portion is applied to the body part; and, wherein the body and the vibrator mechanism are configured to allow the second portion to provide a second vibratory sensation to the user when the second portion is applied to the body part.

In another embodiment, a device for applying vibration to a body part of a user is provided, wherein the body further comprises a neck; wherein the device is configured to allow fingers of the user to engage the neck to maintain the body in a first orientation relative to the fingers of the user to allow the user to apply the first portion to the body part; and, wherein the device is configured to allow fingers of the user to engage the neck to maintain the device in a second orientation relative to the fingers of the user to allow the user to apply the second portion to the body part.

In another embodiment, a device for applying vibration to a body part of a user is provided, the device further comprising a controller, a power source, and a user control; wherein the controller is in communication with the vibrator mechanism; wherein the vibrator mechanism comprises a motor; wherein in the power source provides electrical power for the vibrator mechanism; and, wherein the user control is in communication with the controller, and wherein the user control allows the user to control the vibrator mechanism.

In another embodiment, a device for applying vibration to a body part of a user is provided, the device further comprising a tether attached to the body, wherein the tether is selected from the group consisting of a hand harness, a hand brace, a glove, and a cock ring.

In another embodiment, a device for applying vibration to a body part of a user is provided, wherein the user can control the vibrator mechanism by turning the vibrator mechanism on to provide vibrations when the body is applied to a body part; wherein the user can control the vibrator mechanism by turning the vibrator mechanism off to stop providing vibration when the body is applied to the body part; and, wherein the user can control the vibrator mechanism to provide different vibrating sensations when the body is applied to the body part.

In another embodiment, a device for applying vibration to a body part of a user is provided, wherein the body part is a clitoris, and wherein the body and the neck are configured to allow a female user to use the device while the user's arms and fingers are in natural orientation.

In yet another embodiment, a device for stimulation of a body part of a user is provided, the device comprising: a vibrator mechanism; a body enclosing the vibrator mechanism, wherein the body includes a neck; and, a tether, wherein the tether includes a band, wherein the tether is attached to the body; wherein the body and the tether are configured to allow fingers of the user to engage the neck while the fingers are inserted through the band for stability and control of the device when the body is applied to the body part of the user.

In another embodiment, a device for stimulation of a body part of a user is provided, wherein the body further comprises a fastening mechanism; wherein the tether further comprises an attachment mechanism; and, wherein the attachment mechanism and the fastening mechanism are configured to allow the body to rotate relative to the tether without detaching the body from the tether.

In another embodiment, a device for stimulation of a body part of a user is provided, wherein the body further comprises a first portion and a second portion; and, wherein the body and the vibrator mechanism are configured to allow the first portion to provide a first sensation to the user when the first portion is applied to the body part; and, wherein the body and the vibrator mechanism are configured to allow the second portion to provide a second sensation to the user when the second portion is applied to the body part; wherein when the body is attached to the tether, the attachment mechanism and the fastening mechanism are configured to allow the body to be securely maintained in a first orientation relative to the tether to allow the user to apply the first portion to the body part; wherein when the body is attached to the tether, the attachment mechanism and the fastening mechanism are configured to allow the body to be securely maintained in a second orientation relative to the tether to allow the user to apply the second portion to the body part; and, wherein the attachment mechanism and the fastening mechanism are configured to allow the user to rotate the body from the first orientation to the second orientation.

In another embodiment, a device for stimulation of a body part of a user is provided, wherein the body is shaped like a dildo.

In another embodiment, a device for stimulation of a body part of a user is provided, the device further comprising a controller, a power source and a user control, wherein the controller is in communication with the vibrator mechanism; wherein the vibrator mechanism comprises a motor; wherein in the power source provides electrical power for the vibrator mechanism; and, wherein the user control is in communication with the controller, and wherein the user control allows the user to control the vibrator mechanism.

In another embodiment, a device for stimulation of a body part of a user is provided, the device further comprising a charging circuit, wherein the charging circuit is in communication with the controller and the power source, and wherein the charging circuit allows the power source to be charged when the charging circuit is coupled to an external power source.

In another embodiment, a device for stimulation of a body part of a user is provided, wherein the charging circuit is coupled to the external power source wirelessly.

In yet another embodiment, a device for applying vibration to a body part of a user is provided, the device comprising: a vibrator mechanism; a body enclosing the vibrator mechanism, wherein the body comprises a fastening mechanism, a first portion, and a second portion; and, a tether, wherein the tether comprises a band and an attachment mechanism; wherein the body and the vibrator mechanism are configured to allow the first portion to provide a first vibratory sensation to the user when the first portion is applied to the body part; and, wherein the body and the vibrator mechanism are configured to allow the second portion to provide a second vibratory sensation to the user when the second portion is applied to the body part; wherein the attachment mechanism and the fastening mechanism are configured to allow the tether to be removably attached to the body; wherein the attachment mechanism and the fastening mechanism are further configured to allow the user to rotate the body relative to the tether without detaching the tether from the body; wherein the attachment mechanism and the fastening mechanism are further configured to allow the body to be securely maintained in a first orientation relative to the tether; and, wherein the attachment mechanism and the fastening mechanism are configured to allow the body to be securely maintained in a second orientation relative to the tether; and, wherein the tether and the body are further configured to allow the user to apply the first portion to the body part when the body is in the first orientation relative to the tether; and wherein the tether and the body are further configured to allow the user to apply the second portion to the body part when the body is in the second orientation relative to the tether.

In another embodiment, a device for applying vibration to a body part of a user is provided, wherein the body further comprises a neck; wherein the body and tether are configured to allow fingers of the user to engage the neck while the fingers are inserted through the band when the body is in the first orientation; and, wherein the body and tether are configured to allow fingers of the user to engage the neck while the fingers are inserted through the band when the body is in the second orientation relative to the tether.

In another embodiment, a device for applying vibration to a body part of a user is provided, wherein the fastening mechanism comprises a base and a head; wherein the attachment mechanism comprises an aperture; and, wherein the attachment mechanism and the fastening mechanism are configured to allow the tether to be removably attached to the body by inserting the fastening mechanism in the aperture to allow the aperture to engage the base.

In another embodiment, a device for applying vibration to a body part of a user is provided, wherein the base comprises a cross section; and, wherein the aperture and the cross section of the base have substantially similar shapes and substantially similar sizes; and, wherein when the body is positioned in the first orientation and in the second orientation the aperture and the cross section of the base are aligned and similarly oriented.

In another embodiment, a device for applying vibration to a body part of a user is provided, wherein the shapes of the cross section of the base and of the aperture are elliptical.

In another embodiment, a device for applying vibration to a body part of a user is provided, wherein the shapes of the cross section of the base and of the aperture are polygonal.

In another embodiment, a device for applying vibration to a body part of a user is provided, wherein the body part is a clitoris, and, wherein the body and the tether are configured to allow a female user to use the device while the user's arms and fingers are in natural orientation.

BRIEF DESCRIPTION OF THE SEVERAL VIEWS OF THE DRAWING

The advantages and features of the present invention will be better understood as the following description is read in conjunction with the accompanying drawings, wherein.

DETAILED DESCRIPTION OF THE INVENTION

Figure 1:
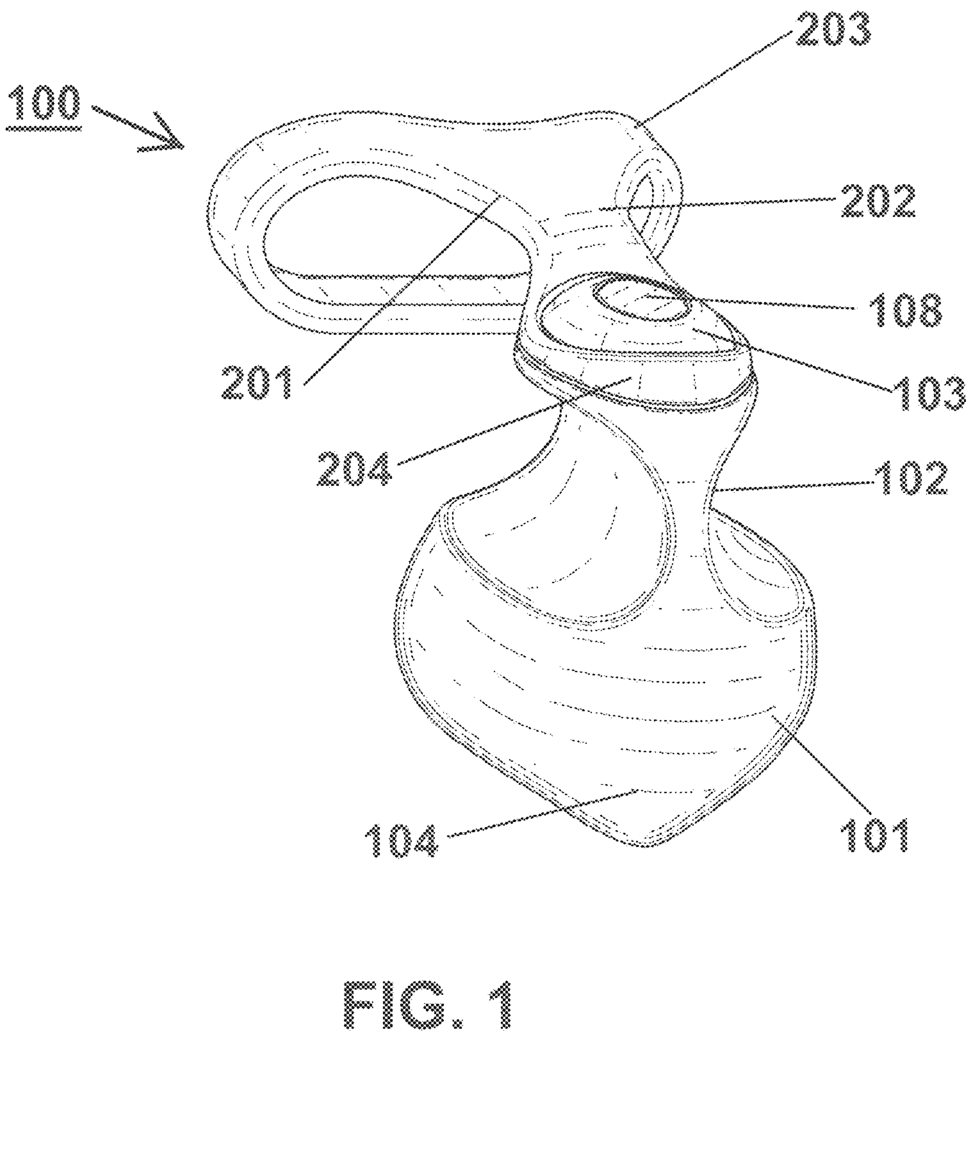
FIG. 1 is a perspective view of a finger vibrating device.
Figure 2:
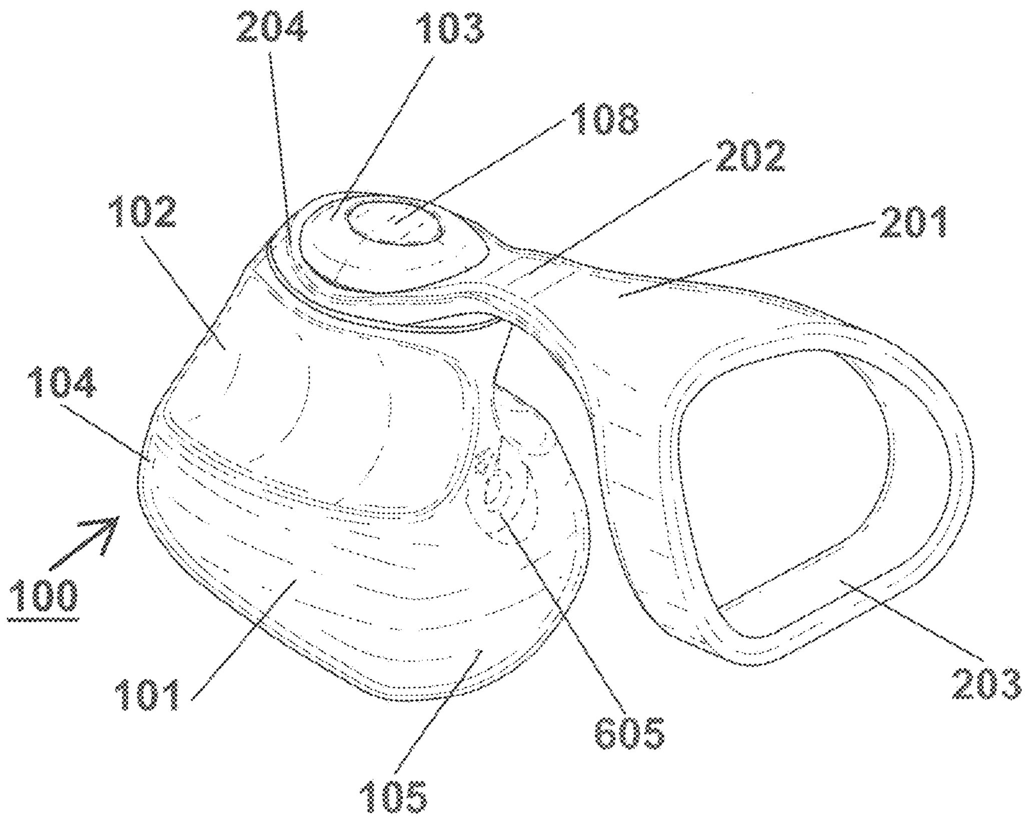
FIG. 2 is a perspective view of a finger vibrating device.

Described herein are devices and methods for applying vibration to a body part of a user, more specifically to finger vibrating devices designed to stimulate the clitoris. Various embodiments are described below in reference to a finger vibrator designed to stimulate the clitoris of a user. Such description is non-limiting, and it will be understood that the finger vibrating devices of the present invention may be utilized to stimulate, apply vibration to, or to massage any body part of a user, including without limitation fingers, hands, eyes, temples, neck, scalp, gums, lips, forehead, face, penis, and any other body part. Various embodiments are also described in reference to a user applying the finger vibrator of the present invention to his or her own body parts, but it will be understood, that the present invention enables a user to apply vibration to or to massage a body part of another person using the finger vibrator of the present invention. The device may be applied to a body part, or used to apply vibration to a body part, by bringing the device in contact with the body part, by positioning it in close proximity with the body part, by inserting it into a body cavity, by applying the vibration to another object (e.g., finger, another body part, device cover, external object, etc.), which in turn is brought in contact with or in close proximity to the body part. As an example, referencing a female user, the user's fingers may contact one body part (e.g., the clitoris) while another body part (e.g., the vaginal opening) is in contact with the device if the user has moved the device closer to the user's fingertips or farther away (e.g., closer to, or in, the user's palm). The device also may be used to apply vibration to a body part in any other method known to a person of skill in the art.

While several embodiments described herein specifically refer to applying vibration to a body part, the devices of the present invention may also be applied to a body and used to stimulate the body part by providing different sensations to the body part, for example, by applying vibration to the body part, by providing a tickling sensation to the body part (for example with a textured cover, such as with ticklers), by generating warmth, by using the device without the vibration turned off to massage or apply pressure, and various other methods of stimulation.

Referring to the embodiments illustrated in FIGS. 1-12, 17, 19 and 20, a device 100 for stimulating a clitoris is shown. The device 100 includes a body 101 generally having a neck 102, a fastening mechanism 103, a user control 108, a front portion 104, a rear portion 105, a vibrator mechanism 601, a power source 602, a controller 603, a transceiver 604, and a port 605. The fastening mechanism 103 comprises a head 106 and a base 107. Device 100 also includes a tether 201 generally having a leash 202 and a band 203. While for readability the embodiments described herein refer to "front portion 104" and "rear portion 105," it will be understood that this nomenclature is arbitrary and the front portion 104 and rear portion 105 can interchangeably be referred to as a first portion 104 and second portion 105.

Referring to embodiments illustrated in FIGS. 13-16 and 18, a device 200 for mechanically stimulating a clitoris is shown. Like device 100, device 200 includes a body 101 generally having a neck 102, a fastening mechanism 103, a user control 108, a front portion 104, a rear portion 105, a vibrator mechanism 601, a power source 602, a controller 603, a transceiver 604, and a port 605. The fastening mechanism 103 comprises a head 106 and a base 107. However, unlike device 100, device 200 does not include a tether 201, as the device 200 may be used to stimulate a clitoris without the need of the tether 201.

Figure 7:
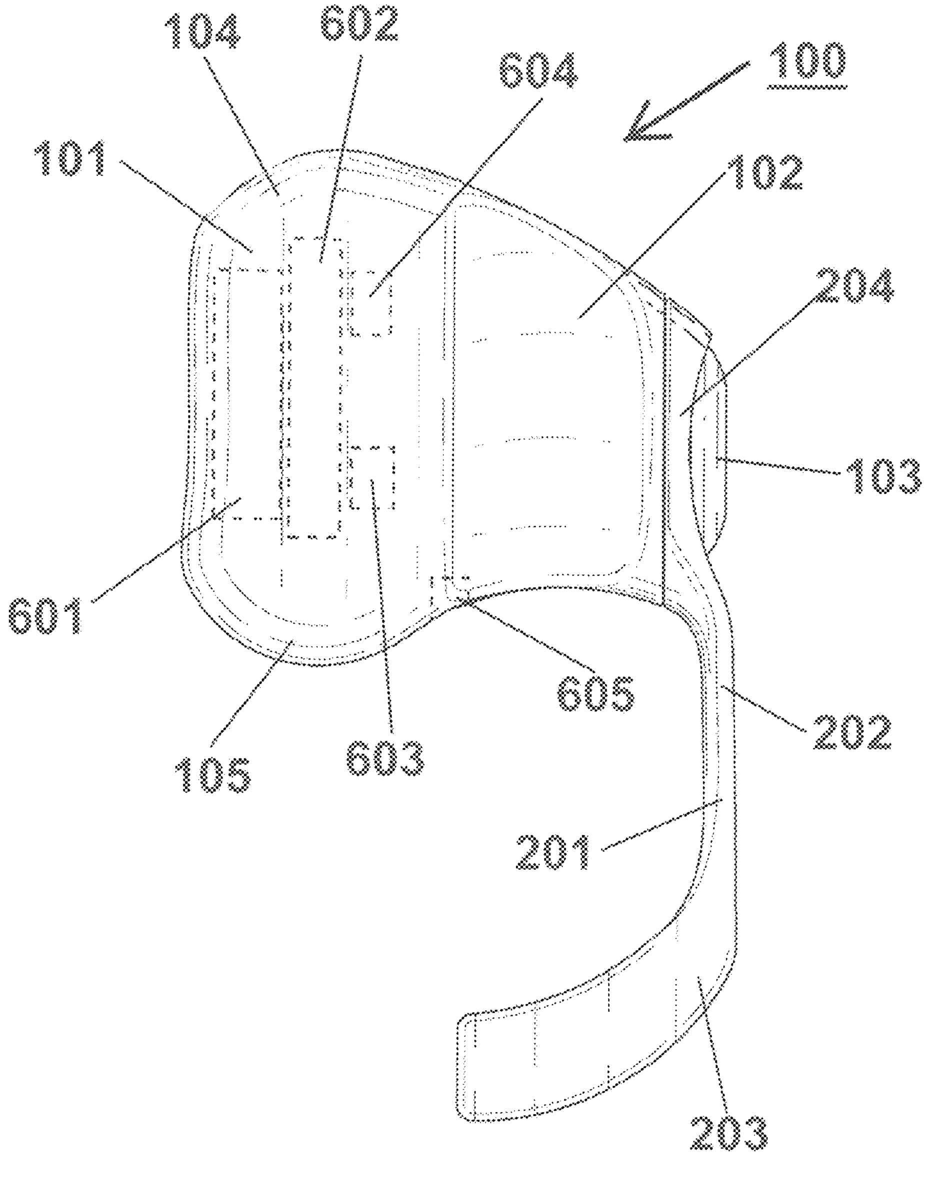
FIG. 7 is a right side view of a finger vibrating device.
Figure 8:
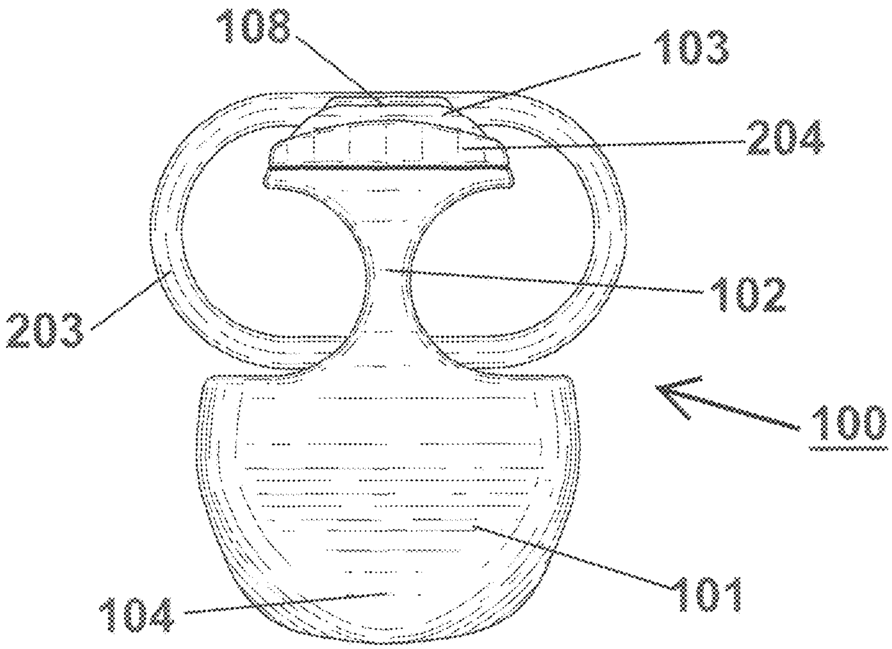
FIG. 8 is a front view of a finger vibrating device.
Figure 9:
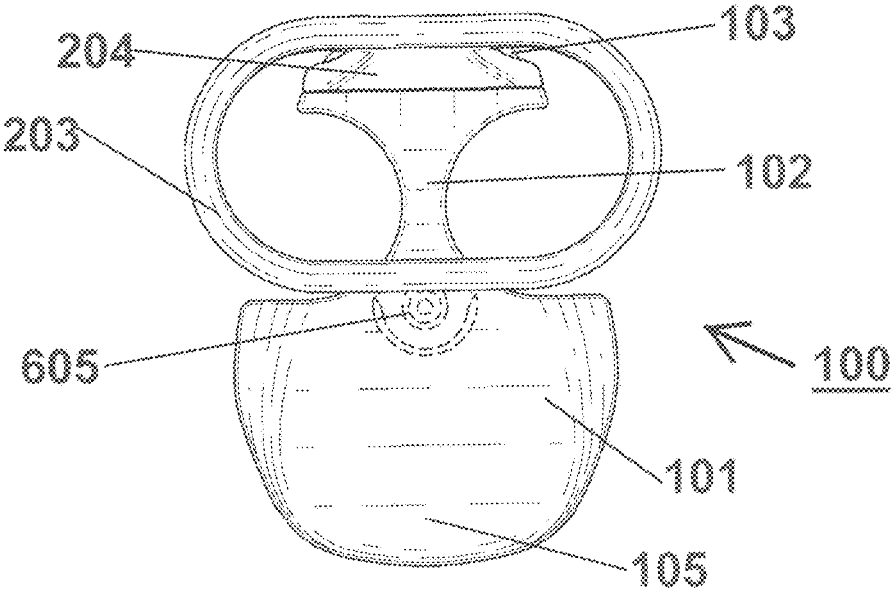
FIG. 9 is a back view of a finger vibrating device.
Figure 10:
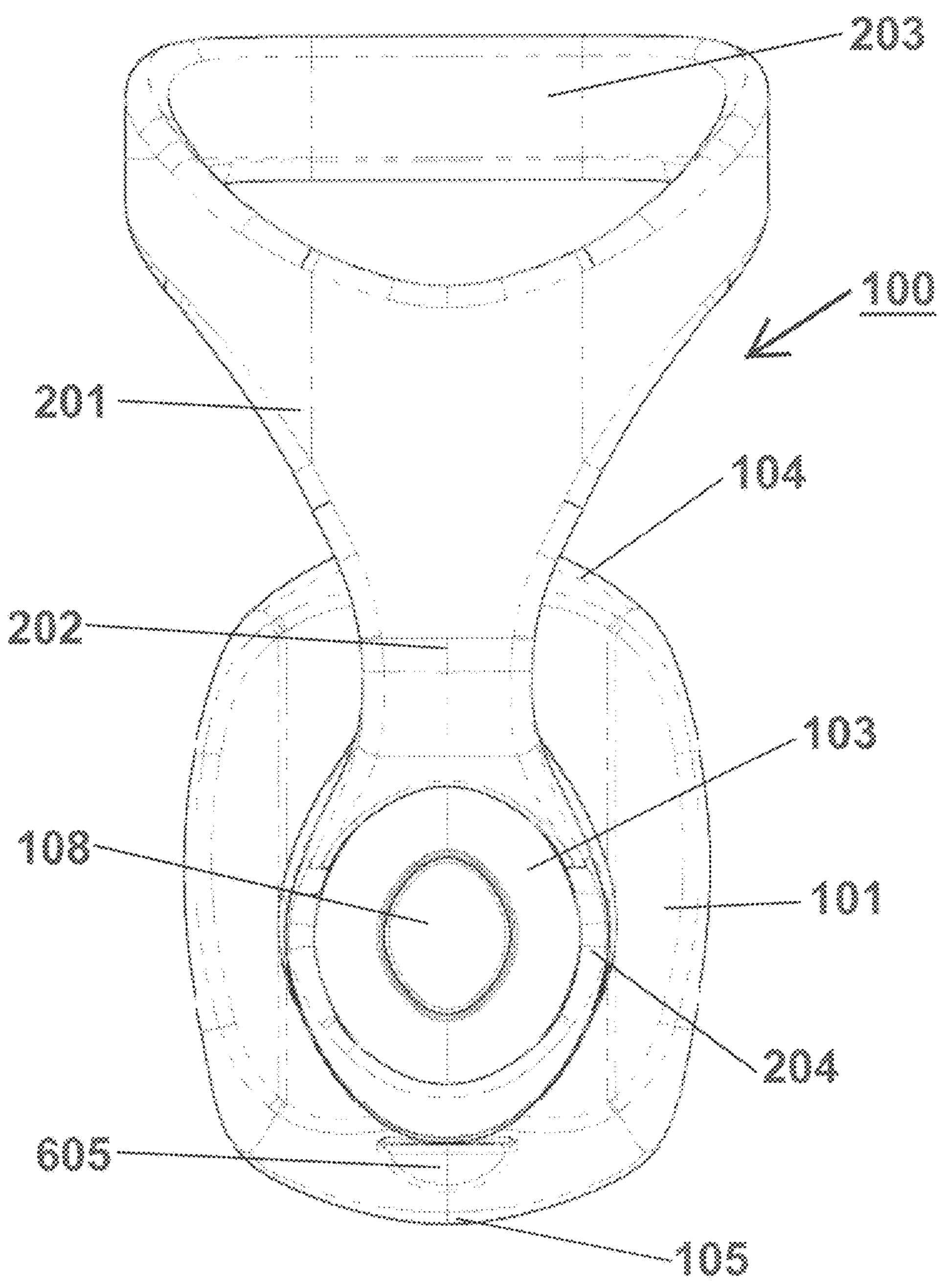
FIG. 10 is a top view of a finger vibrating device with the body rotated 180 degrees compared to FIG. 4.
Figure 20:
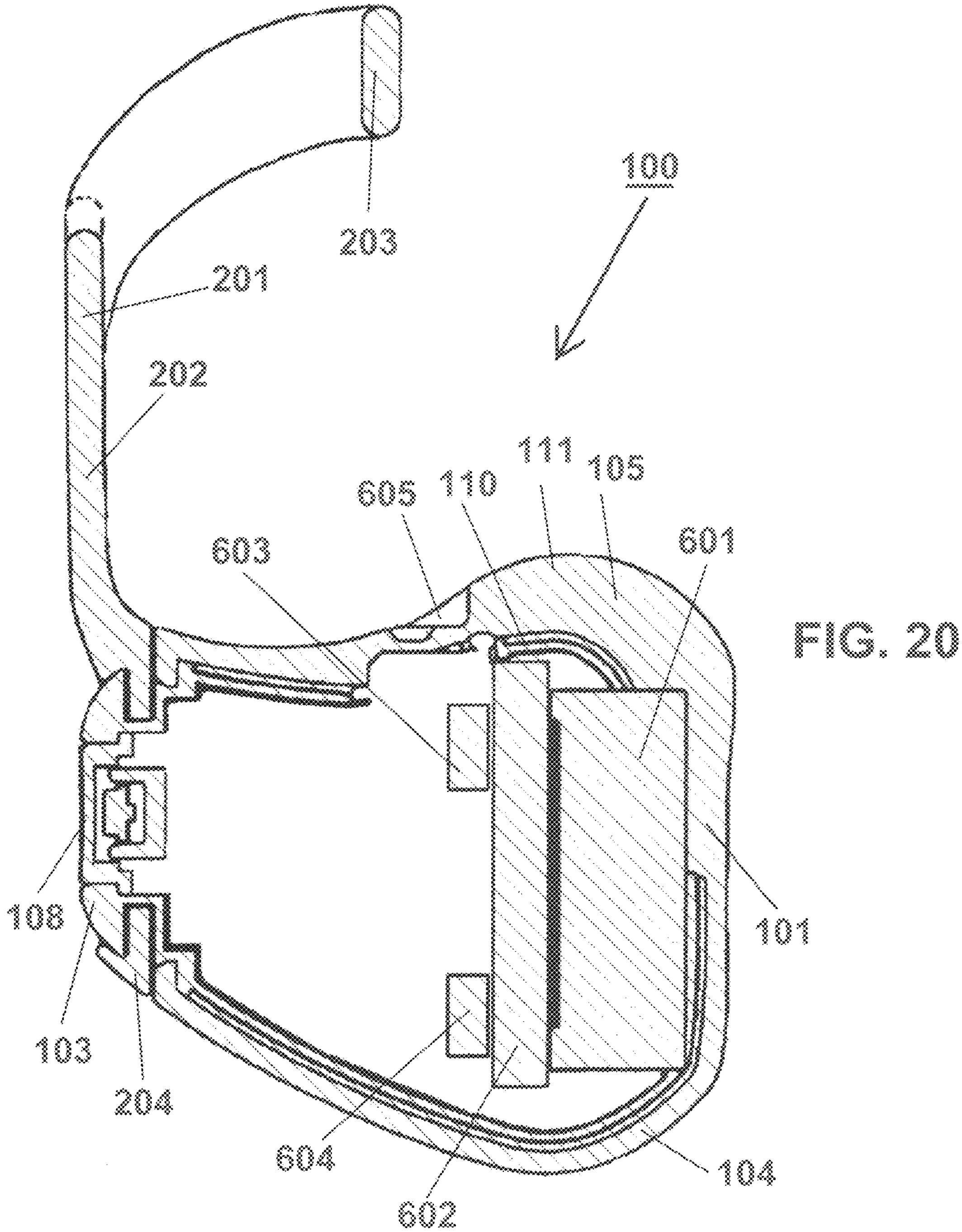
FIG. 20 is a cross-sectional view showing a finger vibrating device for female stimulation.

The vibrator mechanism 601, the power source 602, the controller 603, the transceiver 604, and the port 605 are shown as visible in FIGS. 7 and 20 for the purposes of illustration. However, generally the body 101 of devices 100, 200 encloses the vibrator mechanism 601, the power source 602, the controller 603, the transceiver 604, and the port 605. As explained in detail below, during use, the devices 100, 200 are configured to allow fingers of the user to engage the device 100, 200 for stability and control of the device when the body 101 is applied to the clitoris of the user. Furthermore, during use, the devices 100, 200 are configured where the front portion 104 and the rear portion 105 may be shaped differently, or have different characteristics (e.g., surface texture, vibration dampening material, as described below) so that front portion 104 will provide a first vibratory sensation when applied to the clitoris of a user and rear portion 105 will provide a second vibratory sensation when applied to the clitoris of a user providing the user with varying stimulation experiences when the body 101 is applied to the clitoris. The front portion and the rear portion may also provide different first and second sensations that are not vibratory in nature, or not purely vibratory in nature. For example, the first and second sensations may be tickling, warming, pressure, massage, and other sensations that may be experienced by a user. As will be understood the first and second sensations may also be purely vibratory sensations.

The proportions of the neck 102, fastening mechanism 103, and the size and shape of the device 100, 200 as a whole can be adjusted for use on different body parts, or to accommodate the anatomy of a particular user or group of users. For example, the neck 102 and the fastening mechanism 103 can be configured to project from the body 101 for a sufficient distance to allow fingers of the user to engage the device 100, 200 for stability and control of the device when the body 101 is applied to the clitoris of the user. The neck may also have a stem and a top wherein the top is wider than the stem.

The body 101 of the devices 100, 200 can be formed of a wide range of materials (e.g., rubber, gel foams, plastics, silicone, and/or other suitable materials). In some cases, devices 100, 200 include a base material, e.g., forming an internal enclosure 110, and a coating material encasing the base material and forming a cover 111. The enclosure 110 and the cover 111 can be formed from the same material. Alternatively, the base material and coating material can be different from each other. For example, the base material can be a first material (e.g., nylon, silicone, and/or plastic, non-corroding metal, etc.) while the coating material can be a second material (e.g., medical grade silicone, rubber, gel foams, or plastics). The base materials and/or the coating material are capable of withstanding sanitization methods. For example, the devices 100, 200 can be constructed from a material and in such a manner as to be waterproof and/or water resistant. In other cases, the devices 100, 200 are compatible with automatic cleaning devices (e.g., a dishwasher).

Body 101 may be of various shapes and sizes. For example, in addition to front portions 104 and rear portion 105 that provide vibrations when applied to a body part, body 101 may have a protruding portion suitable for insertion into a body cavity (e.g., vagina). Body 101 may itself be shaped as a dildo (e.g., shaped like an erect penis), which may be attached to tether 201 using fastening mechanism 103. Body 101 may also be shaped with a large flat vibrating portion surface to allow massaging of larger body parts, such as neck, shoulders, musculature, etc.

Body 101 may also accommodate additional removable cover, or sleeves, that alter the sensations experienced by the user, the texture of the surface of body 101, or both. For example, the additional sleeve may be formed of material that is softer, harder, or squishier than the surface of body 101, or it can be made smoother that the surface of body 101, or provide waves, bumps, ridges, ticklers, or other similar protrusions to alter the sensations experienced by the user. The additional sleeve may also be made of material that can be cooled or warmed prior to use to further alter the sensation experienced by the user. The additional sleeve may be shaped to cover the entire surface of body 101, or just a portion of it.

The fastening mechanism 103 includes a head 106 and a base 107. The cross-section of base 107 preferably is elliptical, but may be of any geometric shape, including circle, triangle, symmetric and asymmetric polygons. Preferably the shape of the cross-section of base 107 matches the shape of aperture 205 of tether 201 allowing for secure positioning in one orientation or in a plurality of different orientations as described below. If the cross-section of base 107 is polygonal the angles of the polygon preferably are rounded. Preferably the cross section of head 106 is larger than the cross section of base 107, such that had 106 extends beyond base 107 in at least one direction (as illustrated in FIGS. 3, 13, 14 and 20). The fastening mechanism 103 can be removably attached to the body 101 using screws, clips, pins, or other similar attachment means or fastening mechanism 103 can be made to be an integral part of the body 101, for example by injection molding.

Fastening mechanism 103 can be formed of the same materials as body 101. For example, fastening mechanism 103 can be formed of the same material as enclosure 110 or the same material as the cover 111. Fastening mechanism 103 can also be formed of the same material as tether 201 or fastening mechanism 103 can be formed of a less flexible material. Head 106 may be formed from the same material as the rest of fastening mechanism 103, and base 107. Or head 106 may be formed from different materials than the rest of fastening mechanism 103. Similarly, base 107 may be formed from the same material as the rest of fastening mechanism 103, or it may be formed from different materials than the rest of fastening mechanism 103. The different materials used for head 106 or base 107 may be harder, softer, more rigid, or more flexible than the remainder of fastening mechanism 103.

Figure 3:
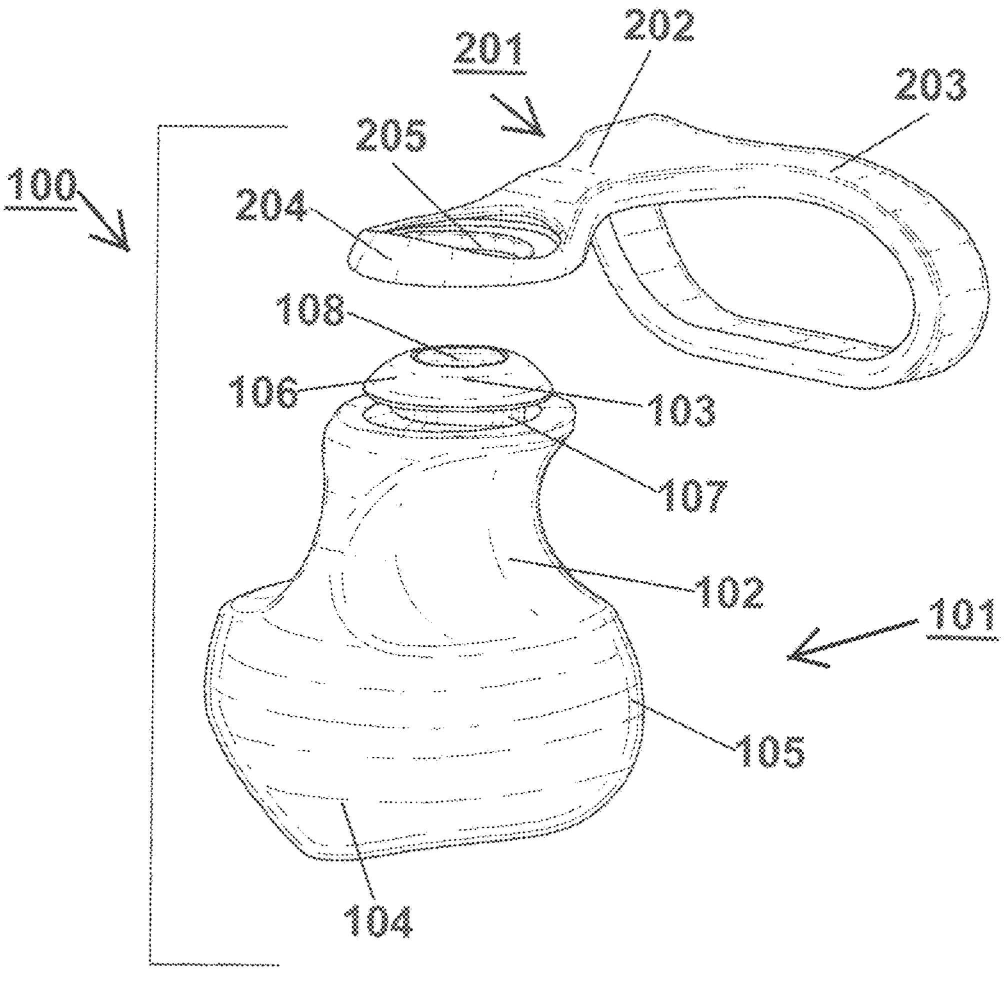
FIG. 3 is an exploded view of a finger vibrating device.
Figure 4:
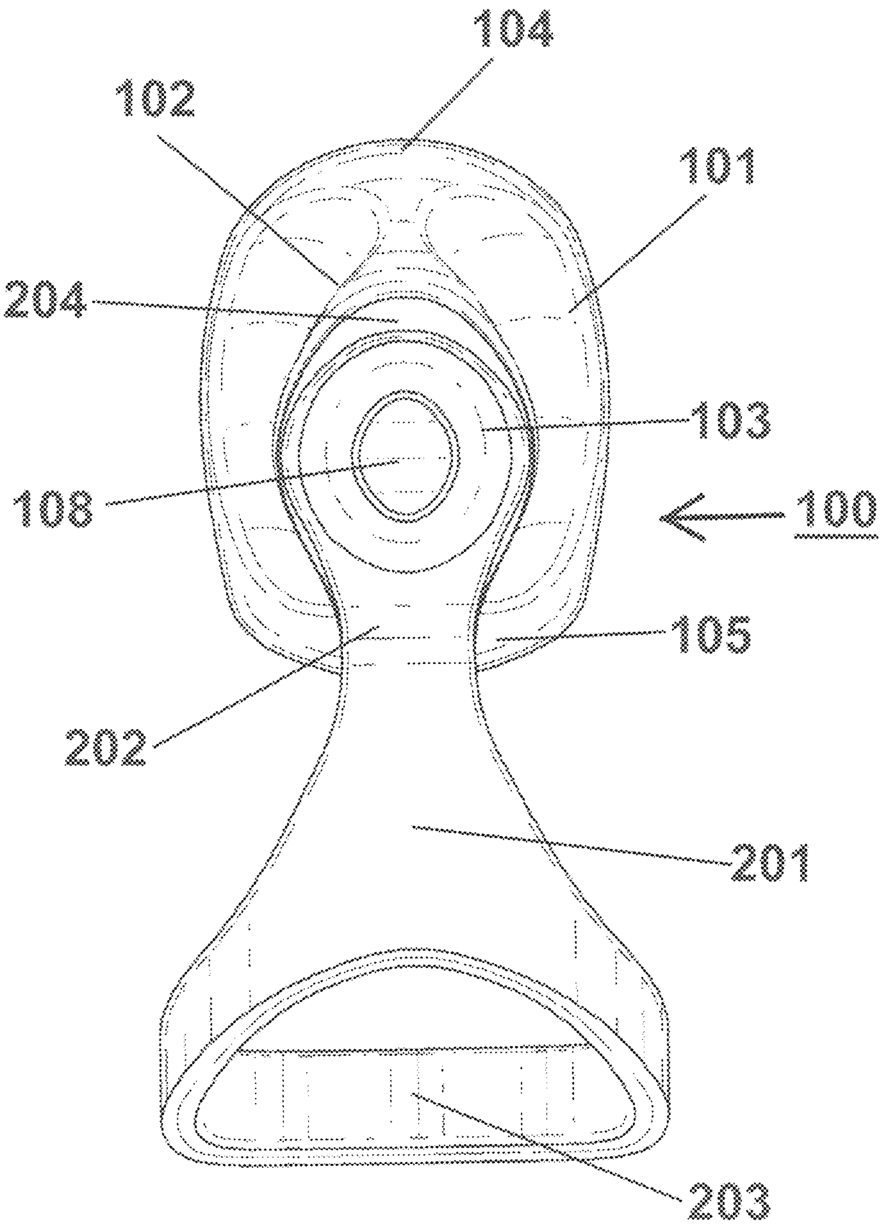
FIG. 4 is a top view of a finger vibrating device.
Figure 5:
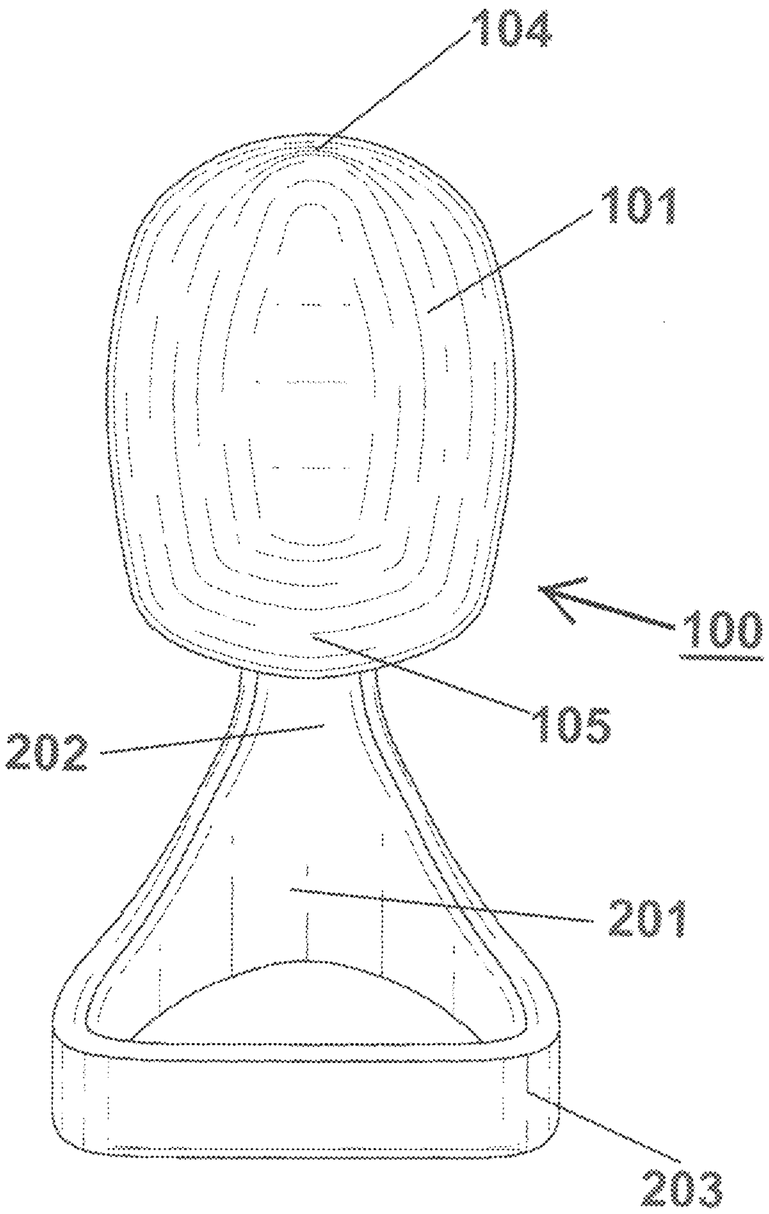
FIG. 5 is a bottom view of a finger vibrating device.
Figure 6:
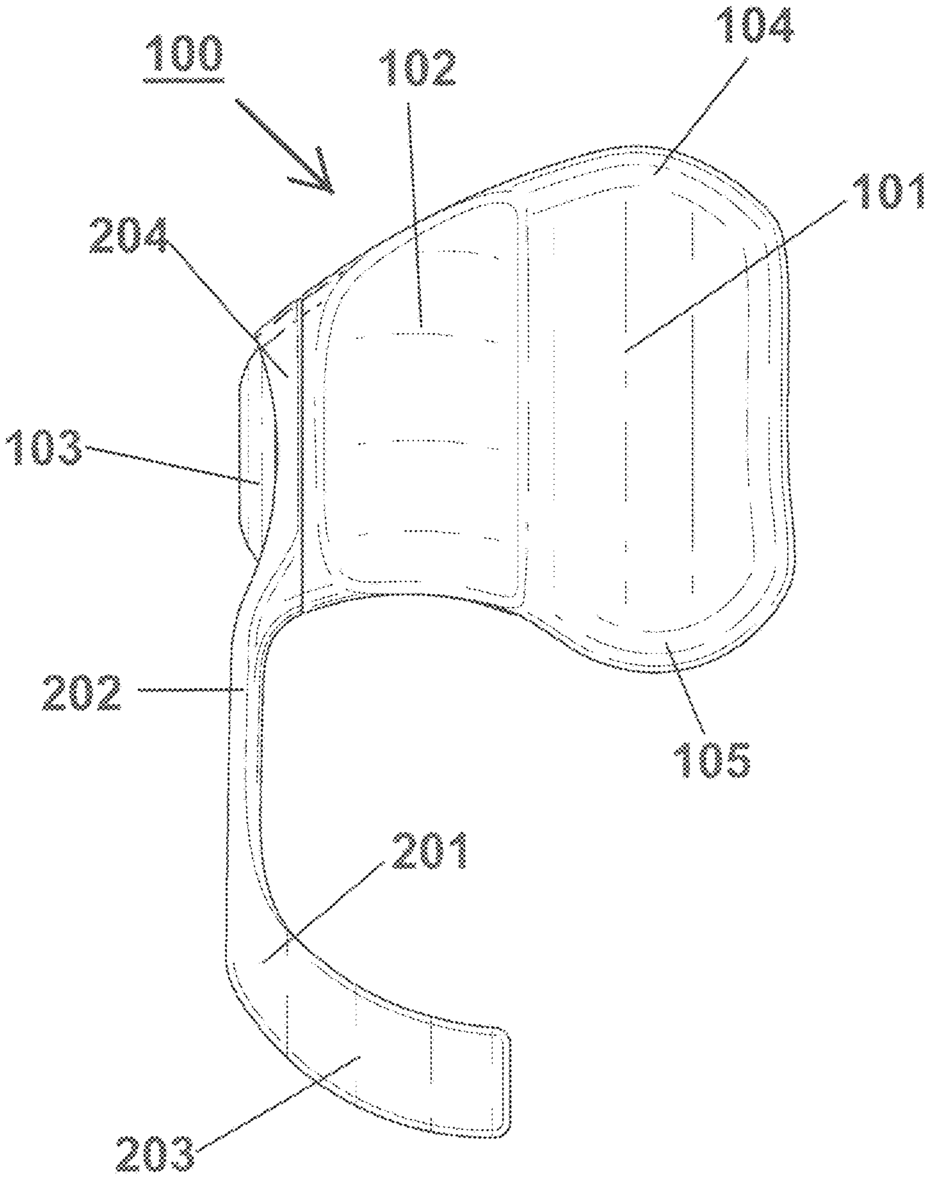
FIG. 6 is a left side view of a finger vibrating device.
Figure 21:
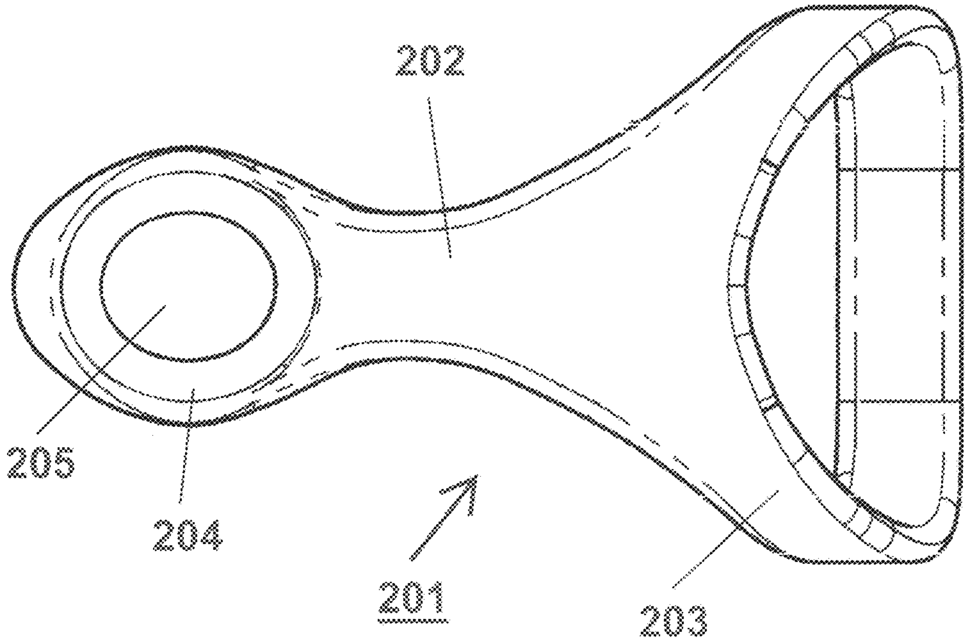
FIG. 21 is top view of a tether for use with the present invention.

Tether 201 includes a leash 202, a band 203 and an attachment mechanism 204 as illustrated in FIG. 21. Attachment mechanism 204 has an aperture 205 of the same or similar shape as the cross-section of base 107 and allows tether 201 to be attached to body 101 using the fastening mechanism 103. Attachment mechanism 204 may be formed of material that is flexible and stretchable. By stretching and flexing attachment mechanism 204 the user can enlarge aperture 205 allowing attachment mechanism 204 to slide over the head 106 and to be positioned encircling base 107 under head 106. By stretching and flexing attachment mechanism 204 a user also can remove tether 201 from the body 101 (as illustrated in FIG. 3) by sliding it over head 106. When the tether 201 is attached to the body 101 and the attachment mechanism 204 is in its relaxed state (in other words, not stretched or flexed), the aperture 205 is smaller than head 106 and the tether 201 cannot be removed unless the user applies sufficient force to stretch the attachment mechanism 204. When the attachment mechanism 204 is in its relaxed state, it is preferable that the size and shape of the aperture 205 are substantially similar to size and shape of the cross section of base 107 allowing the attachment mechanism 204 to engage base 107 and provide a friction fit between attachment mechanism 204 and base 107. To rotate the tether 201 or body 101 relative to each other the user needs to apply a rotational force external to the device 100 to overcome the various forces acting on attachment mechanism 204 while it is engaged to base 107. When no external rotational forces are applied to body 101, tether 201 or both, the body 101 will be securely maintained in a particular orientation relative to tether 201 while aperture 205 engages fastening mechanism 103 and while attachment mechanism 204 is in its relaxed state. For example if the aperture 205 and base 107 are circular primarily friction forces between the attachment mechanism 204 and base 107 secure tether 201 and prevent it from easily rotating relative to the body 101. Circularly shaped aperture 205 and base 107 allow body 101 and tether 201 to be positioned at any orientation relative to each other. If aperture 205 and base 107 are noncircular, in normal use the shapes of aperture 205 and base 107 are in the same orientation and aligned with each other.

Figure 11:
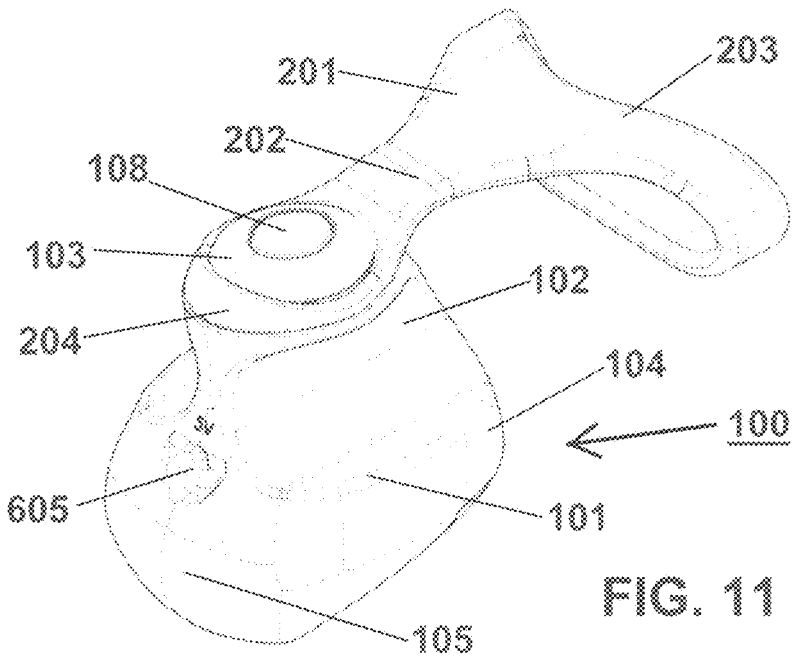
FIG. 11 is a perspective view of a finger vibrating device with the body rotated 180 degrees compared to FIG. 1.
Figure 12:
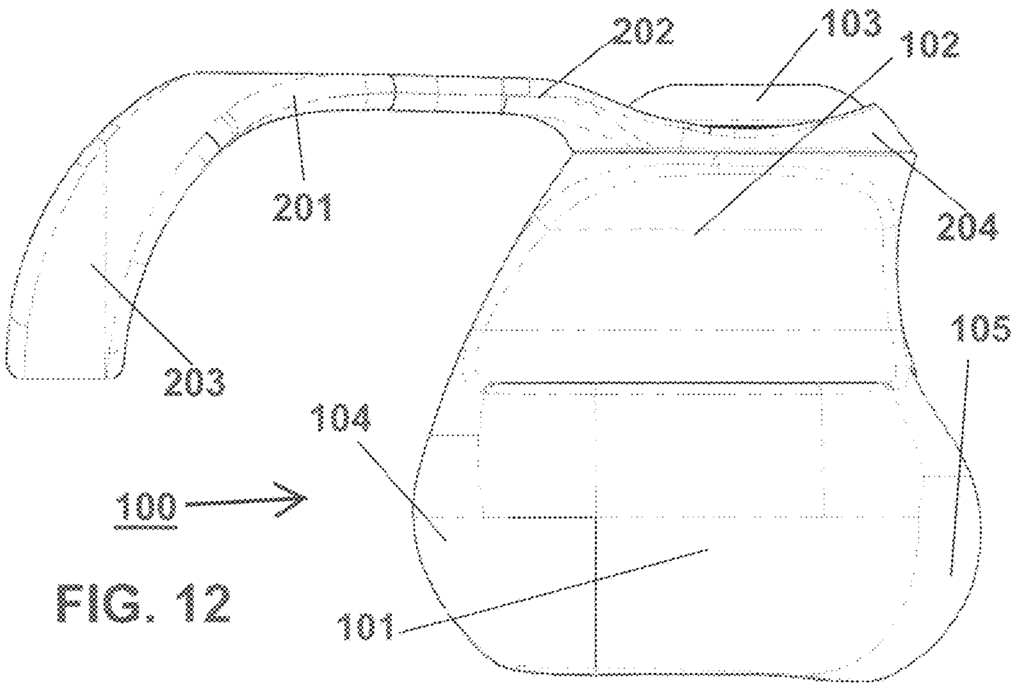
FIG. 12 is a left side view of a finger vibrating device with the body rotated 180 degrees compared to FIG. 6.
Figure 13:
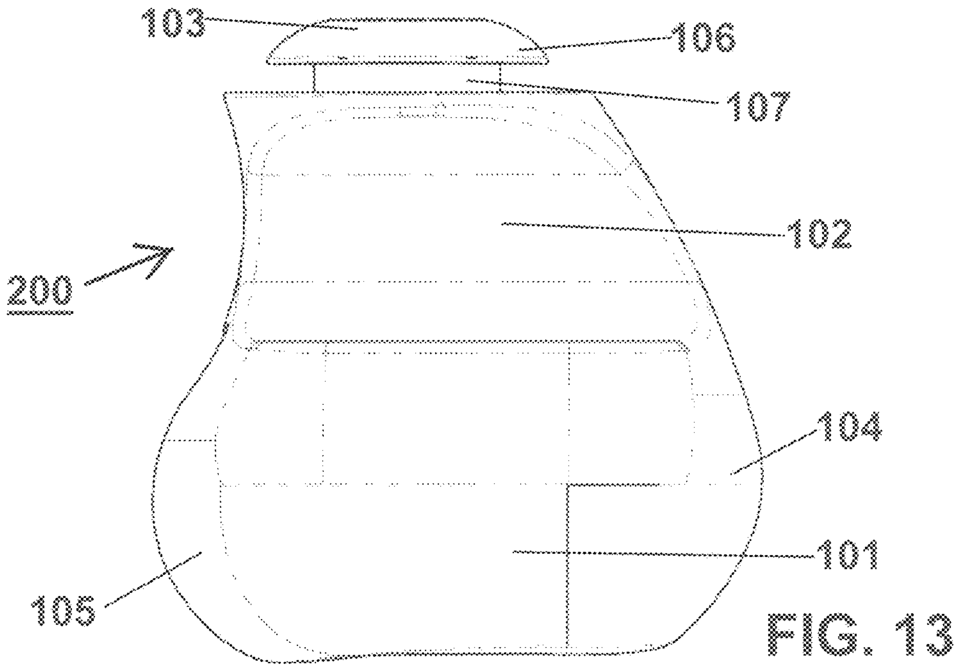
FIG. 13 is a left side view of a finger vibrating device with the tether removed compared to FIG. 6.
Figure 14:
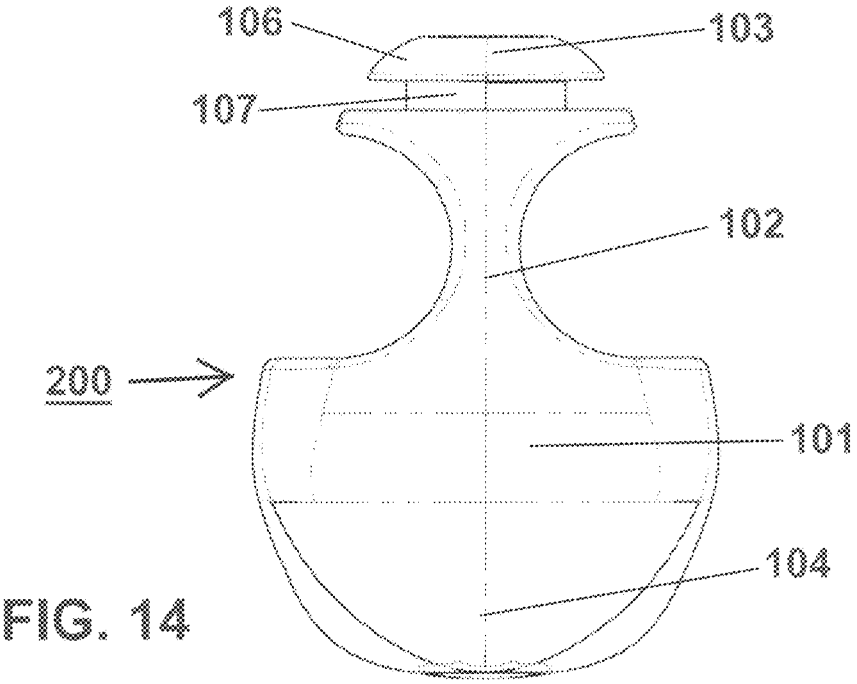
FIG. 14 is a front view of a finger vibrating device with the tether removed compared to FIG. 8.
Figure 15:
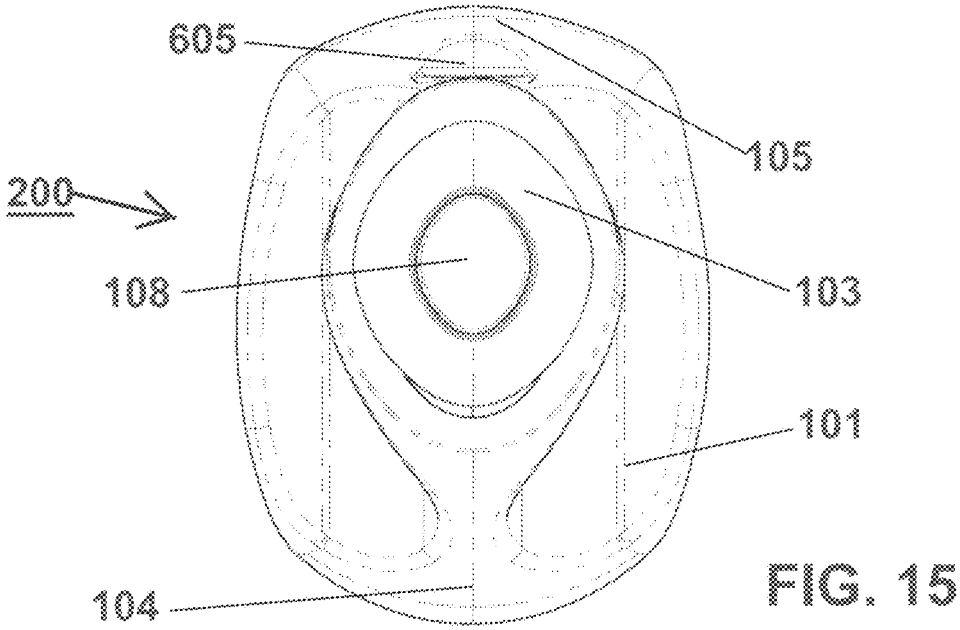
FIG. 15 is a top view of a finger vibrating device with the tether removed compared to FIG. 4.
Figure 16:
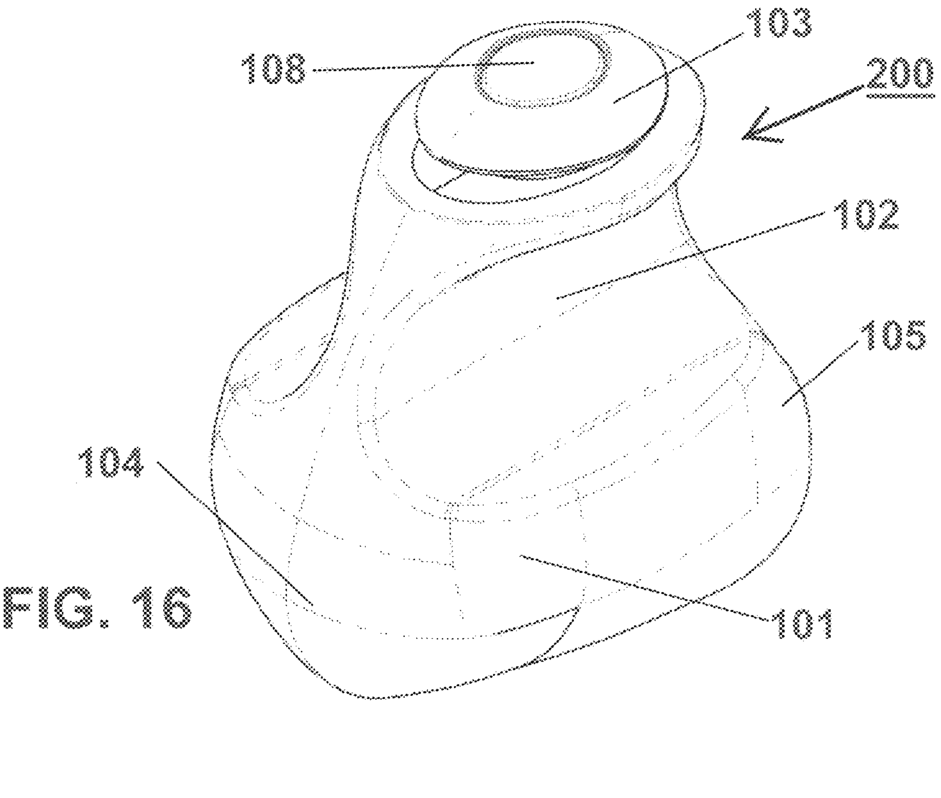
FIG. 16 is a perspective view of a finger vibrating device with the tether removed compared to FIG. 1.

To increase the force required to rotate body 101 relative to tether 201 the shapes of the aperture 205 and the base 107 cross section may be elliptical. It is preferable that the aperture 205 and the cross section of the base 107 have substantially similar elliptical shapes and substantially similar elliptical sizes to provide a friction and interferential fit when the aperture 205 engages base 107. In this embodiment, the major axis of the elliptical aperture 205 and the major axis of the elliptical cross section of the base 107 are of a similar length. Similarly, the minor axes of the elliptical aperture 205 and cross section of the base 107 are also of a similar length. This configuration allows the body to be securely maintained in a particular orientation relative to the tether unless the user applies a sufficient force to rotate the body relative to the tether, or to detach the body from the tether. Elliptical shape allows attachment mechanism 204 and base 107 to be aligned in two positions at 180° from each other permitting the user to rotate the body 101 relative to tether 201 to apply vibration using either the front portion 104 or rear portion 105. The two orientations of the body relative to the tether are illustrated in FIGS. 1 and 11 where in the first orientation shown in FIG. 1 the body is rotated 180 degrees relative to the second orientation shown in FIG. 11. When the body 101 and tether 201 are in the first orientation (FIG. 1) or in the second orientation (FIG. 11) the elliptical aperture 205 and the elliptical shape of the cross section of base 107 are in the same orientation and aligned with each other (i.e., the major axes of the elliptical aperture 205 and the elliptical base 107 are approximately parallel to each other, and the minor axes are also approximately parallel to each other). In addition to the friction fit described above, the elliptical shaped base 107 and aperture 205 also provide an interferential fit, because to rotate the body relative to the tether without detaching it from the tether, the user will have to deform, flex or stretch, the attachment mechanism 204, base 107 or both in order to rotate elliptical base inside the elliptical aperture. Ellipses, is by definition, a geometric shape that is longer than it is wide, or in other words, with a major axis longer than the minor axis.

In another embodiment, to even further secure tether 101 and increase the forces (e.g., friction, interferential) required to rotate it relative to body 101 the shapes of the aperture 205 and the base 107 can be symmetrical or asymmetrical polygons. An added advantage of a symmetrical polygonal shape is that tether 201 and body 101 can be engaged and securely maintained into as many positions relative to each other as there are sides to the symmetrical polygonal shape. Moreover, many other symmetrical and nonsymmetrical shapes are possible for the aperture and cross section of the base within the scope of this invention. It will be understood that when body 101 is being rotated relative to tether 201 under the application of external forces, the attachment mechanism 204 and/or fastening mechanism 103 may be temporarily deformed and or stretched, particularly if the aperture 205 and base 107 are of non-circular shape.

In other embodiments, fastening mechanism 103 and attachment mechanism 204 may be configured to use different methods of attaching the body to the tether. For example, attachment mechanism 204 and/or fastening mechanism 103 may be made of hard enough materials that allow attachment mechanism 204 to snap onto fastening mechanism 103 when body 101 and tether 201 are pressed against each other, instead of stretching and flexing attachment end 204 and/or fastening mechanism 103 to attach them. Attachment mechanism 204 and fastening mechanism 103 may also use clips, or other means to attach body 101 to tether 201. Also, aperture 205 may be an opening through the entire thickness of attachment mechanism 204, or aperture 205 may only be an opening on one surface of attachment mechanism 204 and not go all the way through attachment mechanism 204. Other methods, e.g., spring loaded clips, protrusions on the walls of base 107 or aperture 205, may be used to securely maintain the tether 201 and body 101 in a desired orientation relative to each other. In other examples, head 106 may have a shape substantially similar in shape and size to aperture 205 so as to allow aperture 205 to engage head 106, instead of, or in addition to base 107.

Attachment mechanism 204 may have various shapes to accommodate the fastening mechanism 103. For example, the area surrounding aperture 205 may be recessed so that head 106 is countersunk in attachment mechanism 204. The countersink may be deeper or shallower than head 106, or the countersink can be designed so that head 106 is flush with the top surface of attachment mechanism 204 to provide a pleasing surface and transition. The length of base 107 and the thickness of the of the attachment mechanism 204 material under head 106 and surrounding aperture 205 can be adjusted so that when attachment mechanism and head 106 are engaged the bottom surface of head 106 presses against attachment mechanism 204 and further increases the force necessary to rotate body 101 relative to tether 201.

In a simple embodiment, band 203 may be a strip or loop of material that can wrap around a user's fingers, hand, wrist, arm, head, penis, etc. Band 203 may be formed as an uninterrupted loop or ring so that the user can insert her fingers through band 203, or band 203 may be a strip of material that can be wrapped around user's fingers (or hand, wrist, arm, head, penis, etc.), and secured with a Velcro, clasp, or other securing means that will be known in the art. Band 203 may comprise a single band through which one or more fingers can be inserted, or band 203 may comprise multiple bands, each of which may accommodate one or more fingers. Band 203 may also be large enough to slide over the entire hand of a user so that it can be positioned around the knuckles, around the palm and the top of the hand so that band 203 is between the knuckles and the wrist, or around the wrist.

Leash 202 may be of any length. For example, if band 203 is around a user's wrist, leash 202 can be long enough so that attachment mechanism 204 is positioned under the user's fingers in such a way as to allow the fingers of the user to engage neck 102 when body 101 is attached to tether 201. In this same example, leash 202 may be only so long as to position attachment mechanism 204 (with attached body 101) in the palm of the user's hand. Also, leash 202 may not be present at all (i.e. zero length) so that band 203 and attachment mechanism 204 to be positioned on top of each other. The provision of a tether 201 with a band 203 and a leash 202 that allow the user's fingers to engage neck 102 allow users, and especially female users to use device 100 with the user's arms and fingers in a natural and/or comfortable orientation.

A user may insert one or more fingers through band 203 of tether 201 while using the finger vibrator 100 to hold finger vibrator 100 in a desired location or position. Band 203 may be formed of stretchable and or flexible material so as to allow insertion of different sized fingers or allow insertion of different number of fingers. Moreover, a stretchable band 203 also allows the device to be shared by two people with different sized hands, for example, as a woman and a partner.

The tether 201 can be formed of various materials (e.g., rubber, gel foams, plastics, silicone, and/or other suitable materials). Tether 201 can be formed of the same materials as body 101, or cover 111. Tether 201 can also be formed of different material, for example, flexible shape-memory material while the body 101, and particularly fastening mechanism 103, can be formed of a less flexible material or less compressible material. The band 203, leash 202 and attachment mechanism 204 may all be formed from different materials. For example, band 203 may be formed from an easily stretchable material to accommodate different finger sizes or different number of fingers. The material of band 203 may also be soft to increase user comfort while using device 100. In this example, attachment mechanism 204 may be formed from a harder material that is more difficult to stretch for a more secure attachment to fastening mechanism 103. Leash 202 may be formed from the same materials as attachment mechanism 204, or band 203. Leash 202 may also be formed from a different material with different properties, for example, harder, softer, or more or less flexible, than the other portions of tether 201.

The embodiments described throughout this disclosure illustrate a body 101 with fastening mechanism 103 that may be attached to tether 201 having a band 203, leash 202, attachment mechanism 204 and aperture 205. It will be understood that body 101 and fastening mechanism 103 may also be attached to various other devices or mechanism. For example, body 101 may be attached using the fastening mechanism 103 to a hand brace, a harness, or a glove comprising an attachment mechanism (e.g., an aperture, or a recess, that can accept head 106 and engage base 107)

similar to the mechanism embodied in attachment mechanism 204 having aperture 205. Hand braces are well known, and may include a device that securely wraps around a user's hand (or a portion of a user's hand) to provide support. Hand harnesses are also well known and may include a set of straps, fittings or other devices that attach to, or wrap around, a user's fingers, wrist, or palm to fasten them to another device. Using a similar attachment mechanism body 101 may also be attached to a band that can slide over a penis (e.g., cock ring) for male sexual stimulation or for simultaneous stimulation of the body parts of a couple having intercourse. Body 101 may also be attached to bands of varying sizes, for example a band that can accommodate only a single finger, or a band that can be positioned around the head of a user. It will also be understood that body 101 may be attached in any orientation (e.g., outwards, inwards, sideways, with an offset, etc.) and the size and shape of body 101 may vary to accommodate various applications.

Vibrator mechanism 601 is enclosed within body 101. The vibrator mechanism 601 can provide clitoral stimulation using various techniques and technologies (e.g., vibration, oscillation, electrical stimulation, heat, cooling, sound waves, linear actuation, planar movement of one or more stimulation points, rotary movement of one or more stimulation points, or a combination thereof). Vibration frequency may vary in range from below 1 Hertz (Hz) to ultrasonic vibration. While the vibrator mechanism 601 is generally described as providing vibrations, vibrations are an exemplary technique for providing external sensation to a body part, such as clitoral stimulation.

Vibrator mechanism 601 can cause the body 101 to serve as a vibration mass to contact and to stimulate the clitoris during use where the vibrations are transferred throughout the device 100, 200 thereby causing the body 101 to vibrate against the clitoris. In some cases, a portion of the device 100, 200 can serve as a vibration mass. The vibration can be transferred to selected portions of the device 100, 200. For example, while the body 101 can receive vibrations to function as a vibration mass, the front portion 104 and rear portion 105 have different sizes and shapes, as illustrated in FIG. 20. The differences in sizes and shapes gives the user varying stimulation experiences when the body 101 is applied to the clitoris. For illustrative purposes only in FIG. 20, the rear portion 105 is more rounded, and has more material separating the vibrator mechanism from the surface applied to the user's body part than the front portion 104. The front portion 104 has a more pointed shape and less material separating the vibrator mechanism from the surface applied to the body part. Accordingly the vibrations from the vibrator mechanism 601 will be felt differently through the front portion 104 and the rear portion 105.

In other embodiments body 101 can include multiple vibrating mechanisms to further vary a vibration along different portions of body 101. Furthermore body 101 can have different shapes allowing for multiple portions along the surface of body 101 each portion providing different vibrating sensations for the user when applied to a body part. Different vibrating sensation can be achieved by adding multiple vibrating mechanisms at different positions or with different orientations within body 101, or by using vibrating mechanisms providing vibrations of different frequencies and/or intensities. Different vibrating sensations can also be achieved by varying the amount and/or type of material separating a vibrating mechanism and the outer surface of body 101 being applied to the user's body part. For example heavier material or more material will reduce the intensity of vibrations. Different vibrating sensations can also be achieved by varying the shape of the surface contacting the user's body part. For example pointier shapes that minimize the contact surface between body 101 and the body part will result in a much more intense sensation then more rounded or flatter shapes. It should be understood that numerous mechanisms for producing vibrations and for varying the user sensations would be obvious to one of ordinary skill in the art. For example, while an Eccentric Rotating Mass (ERM) vibration motor (e.g., using an unbalanced mass load to generate vibrations) is generally preferred, pancake or shaftless motors, as well as other means of producing vibratory motion may be used.

The controller 603 is also enclosed in body 101. The controller 603 is configured to control the operation of the vibrator mechanism 601. In this example, the controller 603 switchably connects the vibrator mechanism 601 to the power source 602. The controller 603 may also allow the user to adjust the rate of speed and/or manner of vibration. Alternatively, the device may include a first "ON/OFF" controller for activating and deactivating the vibration-generating motor, and a second "variable speed switch" controller for controlling the rate and/or type of vibration. While the controller 603 is generally shown inside body 101, user controls (e.g., buttons, switches) can be directly or remotely connected to the controller 603. For example, the device 100, 200 includes at least one user control 108 (shown as a button) in communication with the controller 603 to allow the user to control the device 100. The user control 108 can use any of various technologies implementing momentary touch, pressure sensitive, resistive or capacitive touch, resistive or capacitive touchscreens, pressure sensitive touchscreens, knobs, switches, light-sensitive, and sensing mechanisms. Any of these technologies may be adapted to recognize multiple gestures, types of touches, multiple patterns of touches, multiple duration of touch, voice commands, light intensity, and others. By using the user control 108 the user can turn the vibrator mechanism of the device on or off, and the user can control the intensity of vibrations (e.g., by controlling the frequency and amplitude of the vibrations). In one example the device may have a single button as user control 108 that when momentarily pressed sequentially causes the unit to go from off to low, low to medium, medium to high, high to off over the course of four presses of user control 108. Similarly, a longer duration press may interrupt the user control 108 progression and override into some other state such as off, Bluetooth pairing, etc. Various sequences of presses and press durations of user control 108 may be programmed to perform different functions, such as on, off, slow, fast, reset, change operating or vibrating mode, wireless device pairing, etc. Those skilled in the art would appreciate that the user control 108 can be located at a variety of locations on the device 100, 200.

As illustrated in FIGS. 2, 6, 7, 9-13, 15 and 20, a single port 605 is generally shown at near the rear portion 105, those skilled in the art would appreciate that port 605 can be located at a variety of locations on the device 100, 200. Multiple ports may also be provided for performing different functions, such as charging, communications, diagnostic, etc. The device 100, 200 may also include a port cover (not shown) over port 605 to protect the electronic components and provide smooth surface.

The power source 602 used to operate the device 100, 200 (e.g., vibrator mechanism 601, the controller 603, the transceiver 604, or one or more sensors) can be one or more batteries positioned within the body 101. Preferably power source 602 comprises rechargeable batteries that can be charged by connecting the device to an electrical charging device via port 605. Alternatively, other suitable power sources can be used for providing the electrical power to the vibrator mechanism 601, including specific battery types, battery sizes, renewable batteries, rechargeable batteries, disposable batteries). An external power source (such as a wall adapter, USB power, portable external battery) may be connected to port 605, which in turn may be connected to controller 603 and/or a charging circuit (not shown), such that the charging circuit is coupled with the external power source. Port 605 can be a USB port, an electrical charging port, or a communication port. Alternative methods of charging well known in the art such as wireless (e.g., inductive, capacitive) charging may also be used. For example, device 100, 200 may comprise an inductive or capacitive charging circuit and components (e.g., coils, electrical connections, circuits, and other components compatible with the charging circuit) as is known in the art, such that device 100, 200 may be charged by coupling the charging circuit with an external wireless power source (e.g., a charging station connected to a wall power, USB power connection, or similar) by placing the device in or on an inductive or capacitive charger. Device 100, 200 may include charging coils inside body 101 coupled with a charging circuit allowing rechargeable batteries to be charged when the charging circuit is coupled with a wireless charger, for example by positioning device 100, 200 in such a way that the charging coils come in close proximity with an inductive or capacitive charger (e.g., including coils, charging circuits, and electric power connections). Inductive or capacitive charging may utilize industry standards such as "Qi," "A4WP," "PMA," and others.

Device 100, 200 may contain a transceiver 604 (e.g., adapted to communicate with wired or wireless devices, using e.g., Wi-Fi, Bluetooth Near Field Communication ("NFC"), etc.) is contained inside body 101. The transceiver 604 is in electrical communication with the controller 603 and vibrator mechanism 601. The controller 603 may be connected by wired (e.g., via port 605) or wireless connections to a client device (not shown), or to other devices or components. The client device can be a computing device (e.g., mobile devices, desktop computers, laptops, cell phones, personal digital assistants ("PDAs"), iPhones, smartphones, iPads, iWatches, smartwatches, servers, or embedded computing systems), another finger vibrating device, or another sexual stimulation device. Other communication features can include one or more lights, speakers, or tactile feedback mechanisms on the device 100, 200 or external to the device 100, 200. The client device and/or communication features can communicate information related to the state of the device 100, 200, such as on/off, battery status charging, malfunction, additional vibrational modes, current vibrational mode (e.g., low, medium, high), speed, rotations per minute ("RPM"), relative scale of the vibration, and other information related to the device's 100, 200 operation or status.

If a wireless connection is provided, the wireless connection can be configured to provide an essentially real-time information relay between the device 100, 200 and a client device. For example, the client device may display in real-time the current status of the device 100, 200 (e.g., on, off, and/or a specific vibratory pattern or mode). Exemplary low latency wireless connections can be based on an IEEE 802.15 standard, such as the ZigBee communication protocol (other exemplary low latency protocols include ISAIOO.IIa, WirelessHART, and MiWi specification). In another example, the device 100, 200 may communicate through a short-range wireless connection with a computing device, such as using Bluetooth™ technology. The Bluetooth radio transceiver may be integrated into the device 100, 200, as shown, or it may be coupled to the device. The port 605, which may include various communication ports (e.g., USB, Bluetooth, Ethernet, wireless Ethernet) may be coupled to one or more input/output devices, such as a networking device such as a switch or router (e.g., through a network adapter). Using wireless communications the finger vibrator can be synchronized with one or more finger vibrators or other sexual stimulation devices. For example, a command to start, stop or vary the vibration of device 100, 200, may also be wirelessly transmitted to another device allowing multiple devices to operate in synchronization.

In some embodiments, the device 100, 200 includes one or more sensors (not shown) in communication with the controller 603 using a wired or wireless connection to controller 603 or via port 605 or transceiver 604. The one or more sensors can be fully or partially embedded within the device 100, 200 or external to the device 100, 200. The one or more sensors can be used to collect information. For example, the device may make use of one or more image sensors (e.g., CCD, CMOS, or other image sensors), light sensors (e.g., a photo resistor or photodiode), ultrasound sensors (e.g., piezoelectric or magnetostrictive ultrasound sensors), electro dermal activity sensors, force sensors, strain gauges, motion and position sensors (e.g., accelerometers, gyroscopes, or magnetometer), temperature sensors (e.g., thermistors, thermocouples, resistance thermometers, infrared thermometers, or silicon bandgap temperature sensors), sound sensors (e.g., condenser, dynamic, ribbon, carbon, piezoelectric, fiber optic laser, bone conduction, ultrasonic, or MEMS), and/or atmospheric sensors.

The one or more sensors can provide information to the controller 603, or to external device, via the wired or wireless connection. Based, at least in part, on this information, the controller 603 can control the device 100, 200. For example, one or more light sensors can be positioned on the device 100, 200 such that the light sensor can sense the absence or presence of light and communicate this information to the controller 603. The controller 603 can control device 100, 200 operations in response to this information by, for example, automatically activating the device 100, 200 in response to an absence of light. Likewise, the controller 603 can automatically deactivate the device 100, 200 in response to the presence of light. Similarly a microphone or other sound sensor can allow controller 603 to control the device using voice commands.

While the devices and methods generally described position the device 100, 200 to apply vibration to a body part while the fingers of the user engage the device 100, 200 and band 203 for added stability and control of the device 100, 200 without the need for additional devices, additional devices may be employed. For example, straps, gloves, braces, bands, rings, harnesses, or garments (e.g. retention devices) may be employed to assist contact between the device 100, 200 and a body part of a user. The shape of retention devices may be specially adapted to accommodate the shape of the devices, such as with pouches, sized-openings, collars, clips, hooks, latches, buttons, zippers, toggles, anchors, magnets, slots, or keyholes. The retention devices can include material compatible with device insertion, retention, and/or positioning of the retention device.

Additionally or alternatively, the body 101 of the device may provide attachment features such as clips, anchors, slots, depressions, keyholes, or the like adapted to attach and release the device 100, 200 from the retention device. These attachments features can be formed from materials such as natural or synthetic fabric, rubber, plastic, latex, nitrile rubber, hook and loop fastener, silicone, or leather.

In embodiments where the device 100, 200 includes a controller having a physical switch (e.g., user control 108, a switch)), the user may turn the device 100, 200 on and/or select the vibration mode and/or intensity before or during use. In embodiments where the device 100, 200 is remotely controlled (e.g., over Wi-Fi, Bluetooth, NFC), the user may choose to first activate the device 100, 200 before or after applying the device 100, 200 to the clitoris. Alternatively, a remote control may be provided to control device 100, 200 using any wireless communication method. The remote control can be held by the user in a freehand alternatively can be held by another user.

Various vibration patterns are contemplated. For example, the device can include a continuous vibration mode, an intermittent vibration mode, a high intensity mode, a medium intensity mode, a low intensity mode, or an escalating intensity mode. In some examples, the intensity mode is configured to escalate the intensity incrementally over time. By increasing the intensity incrementally, the pattern can mirror the onset of female arousal (e.g., by increasing in intensity in proportion to an increase in arousal).

Figure 17:
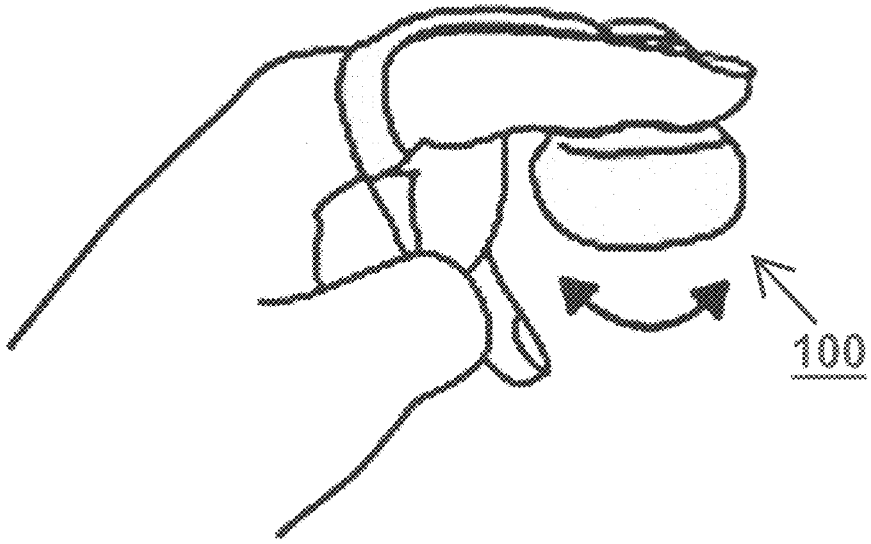
FIG. 17 illustrates an exemplary use of an embodiment of the present invention.

Various exemplary methods of operation of the devices 100 and 200 will now be described with reference to the figures and specifically FIGS. 17-19. Referring to the device 100, where the tether 201 is attached to the body 101, as shown in FIGS. 17 and 19, in operation, the device 100 described herein is held by a user where two of the user's fingers are inserted through the band 203 of the tether 201 and the neck 102 is between the two fingers of the user. The body 101 includes a concave surfaces on either side of the neck 102. The user's fingers rest on these concave surfaces. This embodiment allows the user to engage the device 100 with more stability and control of the device 100.

Figure 18:
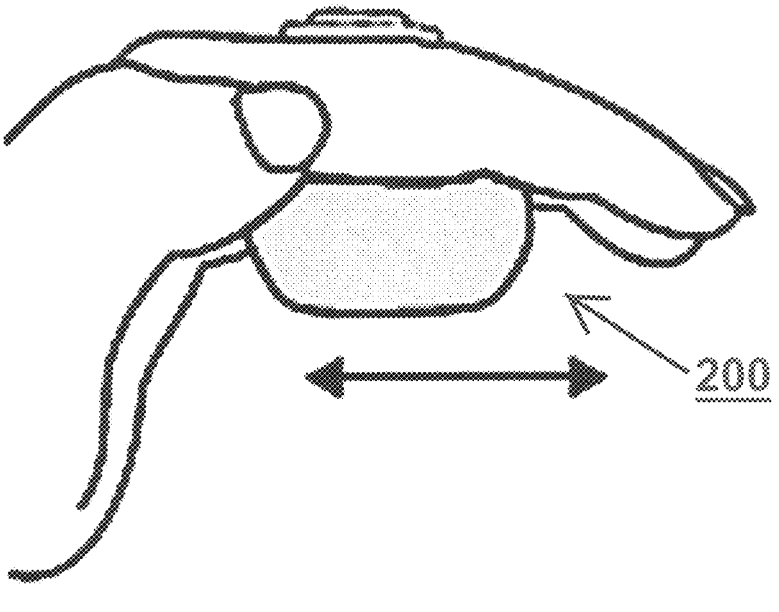
FIG. 18 illustrates another exemplary use of an embodiment of the present invention.
Figure 19:
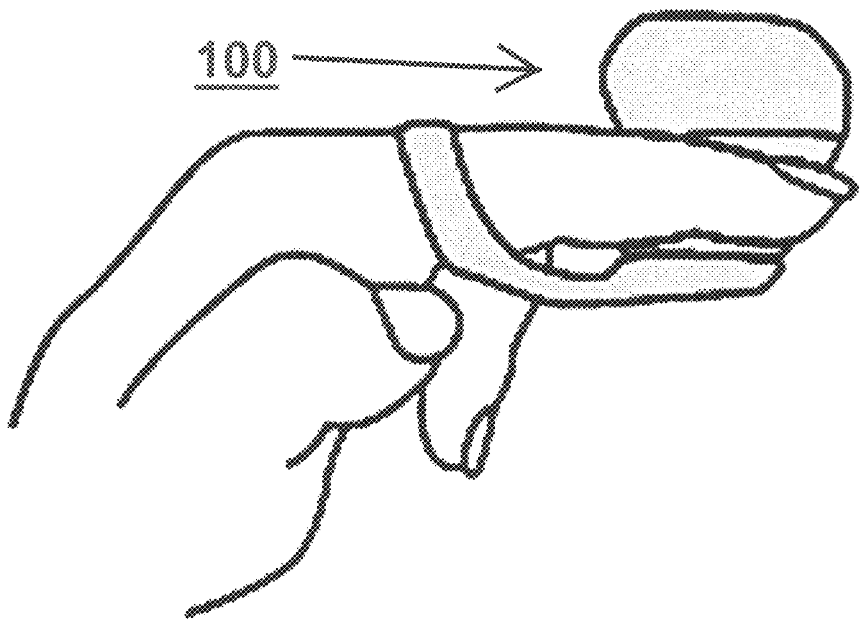
FIG. 19 illustrates another exemplary use of an embodiment of the present invention.

Referring to the device 200 where the tether 201 is not attached to the body 101, as shown in FIG. 18, in operation, the device 200 described herein is held by a user where the neck 102 is between two fingers of the user. The body 101 includes a concave surfaces on either side of the neck 102. The user's fingers rest on these concave surfaces. The device 200 is held where the neck 102 is pressed against where the two fingers meet. This embodiment allows the user to engage the device 100 with stability and control of the device 200. The provision of neck 202 of body 201 allows the user's fingers to engage neck 102 and allow users, and especially female users to use device 200 with the user's arms and fingers in a natural and/or comfortable orientation, In one embodiment device 100 can be converted into device 200 by removing tether 201 from fastening mechanism 103. This reduces the size of the finger vibrator and allows device 200 to be easily carried around in a small pocket or purse. Other benefits of being able to use device 200 without a tether 201 include reduction in time to start and stop using the device (e.g., by eliminating the time needed to insert or remove fingers from band 203 to take the device on or off), eliminating the feeling of restriction of the fingers while the fingers are inserted through band 203 during use, and other benefits.

The device 100 in FIG. 17 is held below the fingers with the fingers engaging the neck of the body of the device while the fingers are inserted through the band of the tether. This allows the user to apply the device 100 directly to the clitoris. With the device 100 rotatably attached to tether 201 in a first orientation, by applying an external rotational force, the device 100 can be rotated to a second orientation without detaching the body from the tether, as illustrated by the two-headed arrow. At the first orientation, for example, the front portion 104 is nearer the finger tips. When the front portion 104 is applied to the clitoris, it provides a distinct stimulation and sensation. Alternatively, at the second orientation the rear portion 105 is nearer the finger tips. When the rear portion 105 is applied to the clitoris, it provides a second distinct stimulation and sensation. With the device 100 being rotatably attached to the tether 201 and the front portion 104 and rear portion 105 having different sizes and shapes, the user may enjoy varying stimulation and sensation experiences when the body 101 is applied to the clitoris of the user.

The device 200 in FIG. 18 is held between the fingers and without the tether 201, the user may slide the device 200 along the length of the fingers (as illustrated by the two-headed arrow) to find the most comfortable spot to hold the device 200. Similar to the device 100 in FIG. 17, the body 101 may be rotated to allow the user to enjoy varying stimulation and sensation experiences when the body 101 is applied to the clitoris of the user.

The device 100 in FIG. 19 is held above the fingers. When the device 100 is operating, the device 100 adds vibrations to the user's direct touch of the clitoris.

The device 100, 200 is configured to allow positioning such that to allow access to the vaginal opening. Thus, the device 100, 200 can be used during intercourse. For example, the body 101 can be positioned and activated to provide stimulation to the clitoris of a user. Simultaneously or separately, the user can participate in sexual intercourse including vaginal penetration by a penis or other object (e.g., a dildo). The devices 100, 200 described herein are then able to provide mechanical stimulation to the external genitalia (e.g., the clitoris of a woman).

Various features of the device 100, 200 (e.g., the vibrator mechanism 601, the power source 602. the controller 603, the transceiver 604, or the port 605) have been omitted from some of the figures for clarity. Each of the features described with reference to the device 100, 200 is contemplated with regards to the other devices 100, 200 described herein.

While a number of exemplary embodiments of the invention have been described, other embodiments are possible. It will be understood by one of ordinary skill in the art that various modifications may be made without departing from the spirit and scope of the invention.

We claim:

1. A device for stimulation of a body part of a user, the device comprising:
- a vibrator mechanism;
- a body enclosing the vibrator mechanism, wherein the body includes a neck; and,
- a tether, wherein the tether includes a band, wherein the tether is attached to the body;
- wherein the body and the tether are configured to allow fingers of the user to engage the neck while the fingers are inserted through the band for stability and control of the device when the body is applied to the body part of the user;
- wherein the body further comprises a fastening mechanism;
- wherein the tether further comprises an attachment mechanism; and,
- wherein the attachment mechanism and the fastening mechanism are configured to allow the body to rotate relative to the tether without detaching the body from the tether.

2. The device of claim 1, wherein the body further comprises a first portion and a second portion; and, wherein the body and the vibrator mechanism are configured to allow the first portion to provide a first sensation to the user when the first portion is applied to the body part; and, wherein the body and the vibrator mechanism are configured to allow the second portion to provide a second sensation to the user when the second portion is applied to the body part;

wherein when the body is attached to the tether, the attachment mechanism and the fastening mechanism are configured to allow the body to be securely maintained in a first orientation relative to the tether to allow the user to apply the first portion to the body part;

wherein when the body is attached to the tether, the attachment mechanism and the fastening mechanism are configured to allow the body to be securely maintained in a second orientation relative to the tether to allow the user to apply the second portion to the body part; and, wherein the attachment mechanism and the fastening mechanism are configured to allow the user to rotate the body from the first orientation to the second orientation.

3. The device of claim 1, further comprising:

a controller;

a power source; and, a user control, wherein the controller is in communication with the vibrator mechanism;

wherein the vibrator mechanism comprises a motor;

wherein in the power source provides electrical power for the vibrator mechanism; and, wherein the user control is in communication with the controller, and wherein the user control allows the user to control the vibrator mechanism.

4. The device of claim 3 further comprising a charging circuit, wherein the charging circuit is in communication with the controller and the power source; and, wherein the charging circuit allows the power source to be charged when the charging circuit is coupled to an external power source.

5. The device of claim 4, wherein the charging circuit is coupled to the external power source wirelessly.

6. A device for applying vibration to a body part of a user, the device comprising:

a vibrator mechanism;

a body enclosing the vibrator mechanism, wherein the body comprises a fastening mechanism, a first portion, and a second portion; and, a tether, wherein the tether comprises a band and an attachment mechanism;

wherein the body and the vibrator mechanism are configured to allow the first portion to provide a first vibratory sensation to the user when the first portion is applied to the body part; and, wherein the body and the vibrator mechanism are configured to allow the second portion to provide a second vibratory sensation to the user when the second portion is applied to the body part;

wherein the attachment mechanism and the fastening mechanism are configured to allow the tether to be removably attached to the body;

wherein the attachment mechanism and the fastening mechanism are further configured to allow the user to rotate the body relative to the tether without detaching the tether from the body;

wherein the attachment mechanism and the fastening mechanism are further configured to allow the body to be securely maintained in a first orientation relative to the tether; and, wherein the attachment mechanism and the fastening mechanism are configured to allow the body to be securely maintained in a second orientation relative to the tether; and, wherein the tether and the body are further configured to allow the user to apply the first portion to the body part when the body is in the first orientation relative to the tether; and wherein the tether and the body are further configured to allow the user to apply the second portion to the body part when the body is in the second orientation relative to the tether.

7. The device of claim 6, wherein the body further comprises a neck, wherein the body and tether are configured to allow fingers of the user to engage the neck while the fingers are inserted through the band when the body is in the first orientation; and, wherein the body and tether are configured to allow fingers of the user to engage the neck while the fingers are inserted through the band when the body is in the second orientation relative to the tether.

8. The device of claim 6, wherein the fastening mechanism comprises a base and a head;

wherein the attachment mechanism comprises an aperture; and, wherein the attachment mechanism and the fastening mechanism are configured to allow the tether to be removably attached to the body by inserting the fastening mechanism in the aperture to allow the aperture to engage the base.

9. The device of claim 8, wherein the base comprises a cross section;

wherein the aperture and the cross section of the base have substantially similar shapes and substantially similar sizes; and, wherein when the body is positioned in the first orientation and in the second orientation the aperture and the cross section of the base are aligned and similarly oriented.

10. The device of claim 9, wherein the shapes of the cross section of the base and of the aperture are elliptical.

11. The device of claim 9, wherein the shapes of the cross section of the base and of the aperture are polygonal.

12. The device of claim 7, wherein the body part is a clitoris, and, wherein the body and the tether are configured to allow a female user to use the device while the user's arms and fingers are in natural orientation.

* * * * *